US00PP17561P3

(12) United States Plant Patent
Meilland

(10) Patent No.: US PP17,561 P3
(45) Date of Patent: Apr. 3, 2007

(54) MINIATURE ROSE PLANT NAMED 'MEIDEINIS'

(50) Latin Name: *Rosa hybrida*
Varietal Denomination: Meideinis

(75) Inventor: Alain A. Meilland, Antibes (FR)

(73) Assignee: CP (Delaware), Inc., Wilmington, DE (US)

( * ) Notice: Subject to any disclaimer, the term of this patent is extended or adjusted under 35 U.S.C. 154(b) by 178 days.

(21) Appl. No.: 10/846,863

(22) Filed: May 17, 2004

(65) Prior Publication Data

US 2004/0216196 P1 Oct. 28, 2004

Related U.S. Application Data

(63) Continuation of application No. 10/228,428, filed on Nov. 6, 2002, now abandoned, which is a continuation of application No. 09/573,161, filed on May 19, 2000, now abandoned.

(51) Int. Cl.
*A01H 5/00* (2006.01)

(52) U.S. Cl. ..... Plt./121

(58) Field of Classification Search ..... Plt./121
See application file for complete search history.

(56) References Cited

PUBLICATIONS

Help Me Find Roses [online][retrieved on Jan. 27, 2006]. Retrieved on the Internet <http://www.helpmefind.com/rose/bd.php?2=37> 5 pages.*
UPOV–ROM GTITM, Plant Variety Database, 2005/04, GTI Jouve Retrieval Software, Citation for *Rosa* 'Meideinis'.*

* cited by examiner

*Primary Examiner*—Kent Bell
*Assistant Examiner*—June Hwu
(74) *Attorney, Agent, or Firm*—Buchanan, Ingersoll & Rooney PC

(57) ABSTRACT

A new and distinct variety of rose plant of the Miniature Class is provided which abundantly forms attractive double deep pink blossoms of good color stability. The buds are conical-shaped and very elegant. The growth habit is low compact and bushy. Decorative medium green semi-glossy foliage is formed that contrasts nicely with the deep pink blossoms. Very good disease resistance is exhibited to powdery mildew under greenhouse growing conditions.

1 Drawing Sheet

Figures 1, 2, 3, 4, 5, 6, 7, 8, 9, 10, 11, 12, 13, 14, 15, 16:
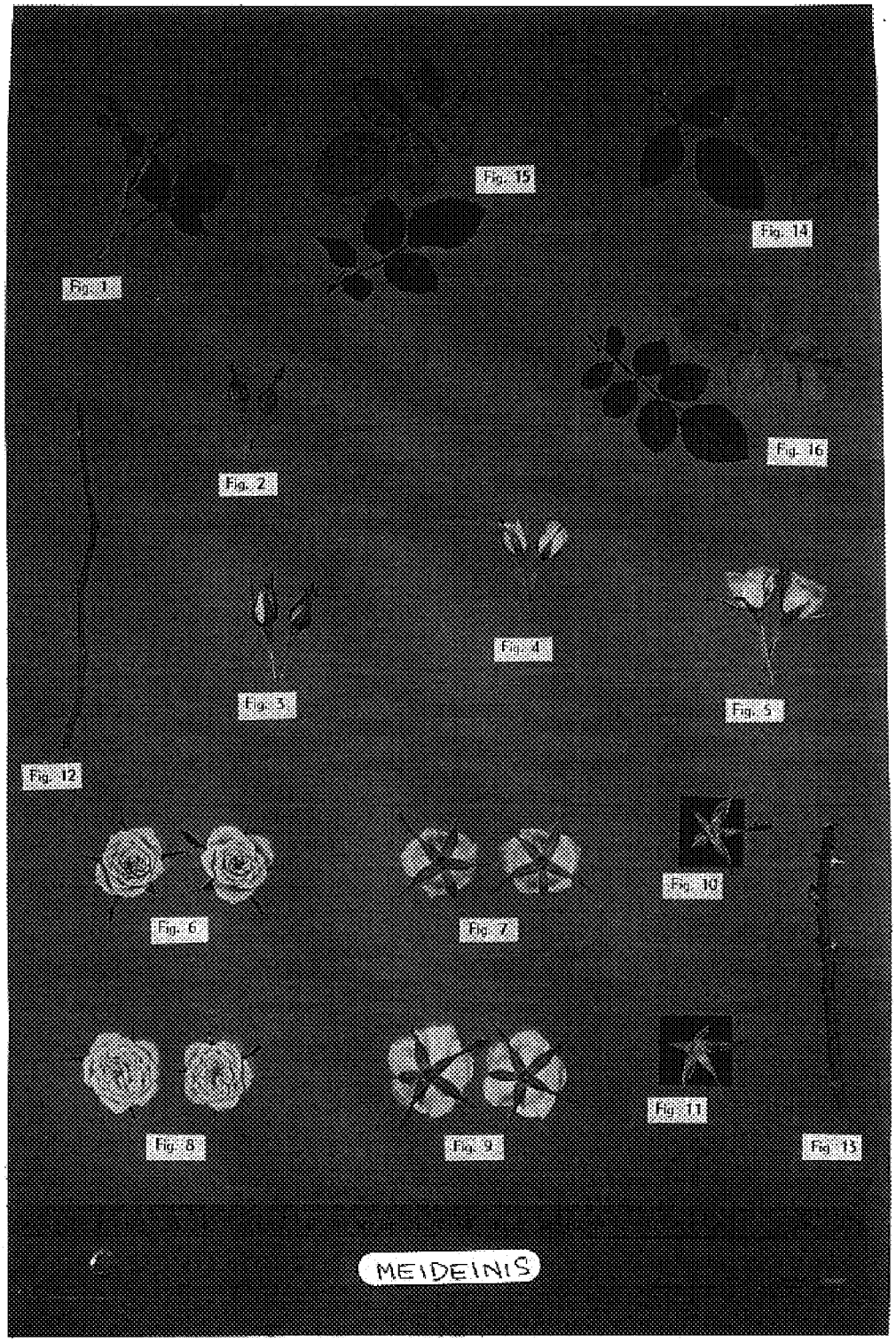

Botanical/commercial classification: *Rosa hybrida*/Miniature Rose Plant.
Varietal denomination: cv. Meideinis.

SUMMARY OF THE INVENTION

The new variety of Miniature rose plant was discovered during 1996 at Cannet des Maures, France while growing among plants of the 'Meirosfon' variety. The new variety is considered to be a spontaneous natural branch mutation of the 'Meirosfon' variety of unknown causation. The blossoms of the new variety displayed a distinctive clear deep pink coloration while those of the parent variety were consistently medium pink in coloration. Also, the parent variety commonly exhibits a shorter height of only approximately 30 to 35 cm at the end of the growing season. Had the new variety of the present invention not been discovered and preserved it would have been lost to mankind.

It was found that the new variety of Miniature rose plant of the present invention possesses the following combination of characteristics:

(a) exhibits a low compact and bushy growth habit,
(b) forms very elegant conical-shaped buds,
(c) forms in abundance attractive double deep pink blossoms of good color stability,
(d) forms decorative dense medium green semi-glossy foliage, and (e) exhibits good resistance to powdery mildew under greenhouse growing conditions.

The new variety well meets the needs of the horticultural industry. It is particularly well-suited for pot forcing under greenhouse growing conditions to form an attractive gift plant.

The new variety of the present invention can be readily distinguished from other Miniature rose varieties, such as the 'Meidarin' variety (U.S. Plant Pat. No. 13,291) and 'Meishulo' variety (U.S. Plant Pat. No. 10,015) in view of the different blossom colorations. More specifically, the 'Meidarin' variety displays bright orange blossoms and the 'Meishulo' variety displays salmon pink blossoms.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another.

The new variety has been named the 'Meideinis' variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were nine months of age and were observed during September while growing on their own roots in greenhouses at LeCannet des Maures, Var, France. Dimensions in centimeters are shown at the bottom of the photograph.

FIG. 1—illustrates a specimen of a young shoot;

FIG. 2—illustrates specimens of two floral buds before the opening of the sepals;

FIG. 3—illustrates specimens of two floral buds at the opening of the sepals;

FIG. 4—illustrates specimens of two floral buds at the opening of the petals;

FIG. 5—illustrates specimens of two flowers during the course of opening;

FIG. 6—illustrates specimens of two open flowers—plan view—obverse;

FIG. 7—illustrates specimens of two open flowers—plan view—reverse;

FIG. 8—illustrates specimens of two fully open flowers—plan view—obverse;

FIG. 9—illustrates specimens of two fully open flowers—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates specimens of two leaves with three leaflets with the under surface being shown at the right and the upper surface being shown at the left;

FIG. 15—illustrates specimens of two leaves with five leaflets with the under surface being shown at the top and the upper surface being shown at the bottom; and FIG. 16—illustrates specimens of two leaves with seven leaflets with the under surface being shown at the top-right and the upper surface being shown at the bottom-left.

DETAILED DESCRIPTION

The chart used in the identification of the colors is that of The Royal Horticultural Society (R.H.S. Colour Chart). The terminology which precedes reference to the chart has been added in some instances to indicate the corresponding colors in more common terms. The description is based on the observation of nine month old specimens of the new variety which were observed during September while growing on their own roots in greenhouses at LeCannet des Maures, Var, France.

Class: Dwarf Miniature.

Plant:

*Height.*—Approximately 30 to 35 cm on average at the end of the growing season.

*Width.*—Approximately 25 to 30 cm at the end of the growing season.

*Habit.*—Bushy.

Branches:

*Color.*—Young stems: near Green Group 143A. Adult wood: near Green Group 137A.

*Texture.*—Young stems: smooth. Adult wood: Smooth.

*Thorns.*—Size: approximately 5 to 6 mm in length. Quantity: moderately sparse as illustrated. Color: near Yellow-Green Group 152D on young stems and tan, near Greyed-Orange Group 175C, on adult wood. Configuration: rather elongated on the upper surface and slightly concave on the under surface.

Leaves:

*Size.*—A five-leaflet leaf commonly is approximately 9 cm in length on average, and approximately 5 cm in width on average.

*Petioles.*—Upper surface: Smoothj, non-glandular, and pale green, near Green Group 138B. Under surface: without prickles and darker green, near Green Group 137A. Length: approximately 4 cm on average.

*Rachis.*—Texture: smooth. Color: near Green Group 138B on the upper surface and near Green Group 137A on the under surface.

*Stipules.*—Smooth, adnate, pectinate, and approximately 1 cm in size.

*Leaflets.*—Number: 3, 5, 7. Shape: commonly with an acute tip and a broad base. Sometimes the tip is cuspidate. Length: a terminal leaflet commonly measures approximately 3 cm in length on average. Width: a terminal leaflet commonly measures approximately 2 cm in width on average. Texture: smooth. Serration: minutely serrated. General appearance: dense, medium green, and semi-glossy foliage. Color (young foliage): Upper surface: near Green Group 137A with some anthocyanin coloration of Greyed-Red Group 178B. Under surface: near Green Group 138B with some anthocyanin coloration of Greyed-Red Group 178B. Color (adult foliage): Upper surface: near Green Group 139A. Under surface: near Green Group 137C.

Inflorescence:

*Number of flowers.*—Commonly approximately 2 to 5 per stem.

*Peduncle.*—Smooth, long and rigid, the length is approximately 5.5 cm on average, and the color is near Green Group 143B.

*Sepals.*—Upper surface: near Green Group 137D. Under surface: near Green Group 143A. Shape: elongated, commonly without extensions (as illustrated) and approximately 2 to 3 cm in length on average. Texture: smooth on the under surface and slightly tomentose on the upper surface.

*Buds.*—Shape: conical. Length: approximately 1.5 cm on average. Diameter: approximately 1 cm on average. Size: medium for class. Texture: physically firm.

*Flower.*—Form: double, petals arranged in a whorl, and cup-shaped. Diameter: approximately 3.5 to 4 cm on average when fully open. Color (when opening begins): Upper surface: Red Group 55D and widely suffused with Red Group 55B. Under surface: near Red Group 55C. Color (when blooming): Upper surface: Red Group 55D and widely suffused with Red Group 55B. Under surface: near Red Group 55C. Color (at end of opening): Upper surface: near Red Group 55D and widely suffused with Red Group 55B. Under surface: near Red Group 55C. Petal spot at base: present on both surfaces and near Orange-White Group 159C in coloration. Petal number: approximately 46 to 48 on average. Petal margin: slightly undulated and reflexed. Petal configuration: rounded tip and a wedge-shaped base. Petal texture: typical for a miniature rose. Petal size: external petals commonly are approximately 1 to 1.5 cm in length on average and internal petals commonly are approximately 0.5 to 0.9 cm in length on average. Petaloids: none. Fragrance: none. Anthers: near Yellow-Orange Group 20A in coloration. Stamen number: approximately 32 on average. Stamen size: approximately 3 mm in length. Filaments: near Yellow Group 5C in coloration. Pollen: pale yellow in coloration. Pistil number: approximately 33 on average. Pistil size: approximately 3 mm in length. Stigmas: near Orange-White Group 159C in coloration. Styles: Greyed-Yellow Group 160C with some Red-Purple Group 63C in coloration just below the stigma. Receptacle: smooth, greenish in coloration, near Green Group 143A, approximately 5 to 6 mm in length and approximately 3 to 4 mm in width, and in longitudinal section in the shape of a funnel. Lasting quality: very long and approximately 10 days on average on the plant. Petal drop: good, the petals detach well.

Development:

*Vegetation.*—Very strong.

*Blooming.*—Very abundant.

*Resistance to diseases.*—Good for powdery mildew under greenhouse growing conditions.

*Propensity to form hips.*—None observed during observations to date.

I claim:

1. A new and distinct variety of Miniature rose plant characterized by the following combination of characteristics:

(a) exhibits a low compact and bushy growth habit, (b) forms very elegant conical-shaped buds, (c) forms in abundance attractive double deep pink blossoms of good color stability, (d) forms decorative dense medium green semi-glossy foliage, and (e) exhibits good resistance to powdery mildew under greenhouse growing conditions;

substantially as herein shown and described.

* * * * *

MEIDEINIS